United States Patent [19]

Syers

[11] Patent Number: 5,297,563

[45] Date of Patent: Mar. 29, 1994

[54] GUIDED BONE AND TISSUE GENERATION DEVICE AND METHOD TO BE USED DURING OR AFTER DENTAL SURGERY OR JAW SURGERY

[76] Inventor: Charles S. Syers, 325 Ascot Rd., Hillsborough, Calif. 94010

[21] Appl. No.: 862,894

[22] Filed: Apr. 3, 1992

[51] Int. Cl.⁵ .............................................. A61B 19/00
[52] U.S. Cl. ................................... 128/898; 128/859; 433/229
[58] Field of Search ............................. 128/897–898, 128/859, 861; 433/215, 229

[56] References Cited

U.S. PATENT DOCUMENTS

| 4,533,326 | 8/1985 | Anthony | 433/229 |
| 5,006,071 | 4/1991 | Carter | 433/215 |
| 5,059,123 | 10/1991 | Jernberg | 433/215 |

FOREIGN PATENT DOCUMENTS

| 2-182251 | 7/1990 | Japan | 433/229 |
| 1107856 | 8/1984 | U.S.S.R. | 433/215 |

Primary Examiner—Lee S. Cohen
Assistant Examiner—J. P. Lacyk
Attorney, Agent, or Firm—Townsend and Townsend Khourie and Crew

[57] ABSTRACT

The invention relates generally to methods and devices for facilitation of tissue and bone guided regeneration of a bony deficit. A mechanical barrier dimension to cover the deficit is provided as are means for securing the barrier in place.

7 Claims, 2 Drawing Sheets

GUIDED BONE AND TISSUE GENERATION DEVICE AND METHOD TO BE USED DURING OR AFTER DENTAL SURGERY OR JAW SURGERY

BACKGROUND OF THE INVENTION

The invention relates generally to devices and methods to promote guided bone and tissue healing after occurrence of an inflammatory traumatic or surgical wound. More specifically, the invention relates to the guided healing of a bony deficit of the maxillae or mandible after extraction of an impacted molar tooth or after periodontal surgery, or after fracture repair, or jaw surgery for any reason.

Normally, when a patient's wisdom tooth or molar is removed or when the above surgeries are performed, a surgeon incises a flap of soft tissue in back of, or posterior to, an adjacent tooth so as to visualize the impacted tooth or surgical field. This operation is routine. Sometimes the bone in the field is absent or unhealthy. This problem may be present before the operation or after the surgery is completed. For example, pre-operatively the bone may have begun a resorptive process due to the inflammation or tumor around an impacted third molar or other described injury or deficit.

The oral surgeon attempts to suture the incised tissue flap back together, creating an environment for bone healing. If the bone does not heal properly and regenerate, then the patient may develop a periodontal pocket or an open space in back of the surgerized area. Because this area tends to retain trapped food or become infected, it rarely heals well. Poor bone healing in this circumstance is more prevalent in the older population, but can also occur in young patients.

The dental profession has some experience with a technique called "Tissue Guided Regeneration" or TGR. When the bone does not heal well, i.e., up to its proper level, one factor is the need to protect the proper environment required by the precursor bone cells, called progenitor cells, to form new bone. These multipotential bone cells which form new bone are undifferentiated and demand a specific type of biological medium to form mature bone. This process may take about one or two months. When a surgeon closes a wound, the epithelium in that wound invaginates or creeps into the field that has been created by removing the tooth or performing surgery. The invagination process is very fast, usually taking 7-14 days. Once invagination of epithelium occurs, it is impossible for the progenitor bone cells to occupy this location to create new bone. Thus, the bone healing is compromised, and the level of potential bone growth is not achieved.

SUMMARY OF THE INVENTION

The invention provides a mechanical and biological barrier and means of securing the barrier in position. The barrier is placed over a tissue deficit, such as a bony deficit, so as to provide a shaped coverage. Thus the bony deficit is protected from epithelial invagination until progenitor cells allow bone to regenerate. The barrier may be formed of a resorbable material; alternatively, it can be nonresorbable and thus require subsequent surgical removal.

Once positioned, the barrier is secured or anchored into place by any of the following attachments. Suture material swaged to the barrier membrane could be used. Suture material with a swaged-on needle is useful to anchor the barrier through the soft tissue. Thus, the barrier is slipped into the wound to cover the surgical field or bony defect. The needle is brought underneath the flap and pushed outward through the flap tissue. Preferably two or more sutures with attached needles are provided such that each needle pierces its respective overlying portion of the flap. When the suture is tied together the flap edges are approximated. Thus a barrier is formed between the overlying soft tissue and underlying bony surgical field or defect.

Additionally, a pincer device attached to the edge of the barrier could secure the barrier. The pincer may take several forms. It may be a clamp-like device which grasps a natural structure in the vicinity of the deficit, such as a molar tooth. Alternatively, it may include a harness or bracket which engages a nearby structure, such as an orthodontic bracket, wire, or implant. The pincer could be reinforced with suture material to secure its location or could be spring loaded to prevent its dislodgement.

Additionally, the under surface of the barrier membrane may contain a support foot or support ridge to elevate its position from the field or defect. This will allow more bone regeneration. The foot or ridge could be modified.

BRIEF DESCRIPTION OF THE FIGURES

FIG. 3A is a side view with and without ridge and feet and FIG. 3B is a top view.

DETAILED DESCRIPTION OF A PREFERRED EMBODIMENT

The invention provides methods and devices to facilitate tissue guided regeneration of a bony deficit. The bony deficit may have occurred from a surgical procedure, such as extraction of an impacted molar, or from a traumatic accident or from tumor or inflammatory disease.

Figure 1:
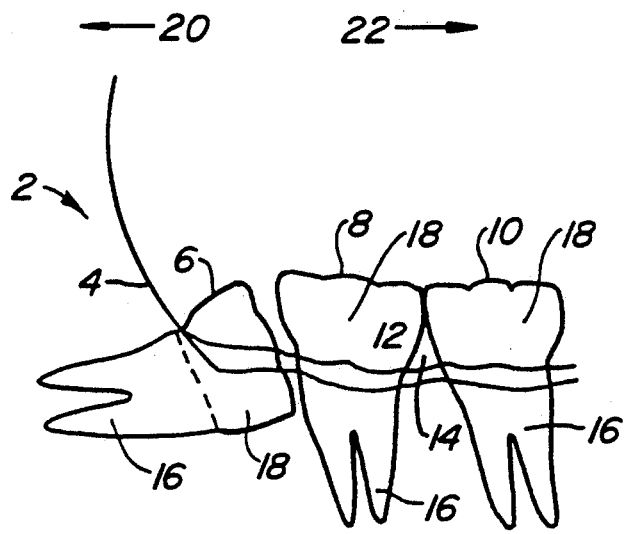
FIG. 1 is a schematic of molars and an impacted wisdom tooth.

Referring to FIG. 1, a schematic of a mandible 2, an impacted wisdom tooth 6, a second molar 8 and a first molar 10 is shown. A root 16 and a crown 18 are components of each tooth. Wisdom tooth 6 is posterior or dorsal to molar 8 as indicated by the direction of arrow 20. An anterior or ventral direction is indicated by the direction of arrow 22. A normal bone line 4 and a normal gum line 12 are depicted. Wisdom tooth 6, being impacted, is not normally erupted. It is locked into position by bone or, in some cases, by a surface of adjacent molar 8.

Figure 2:
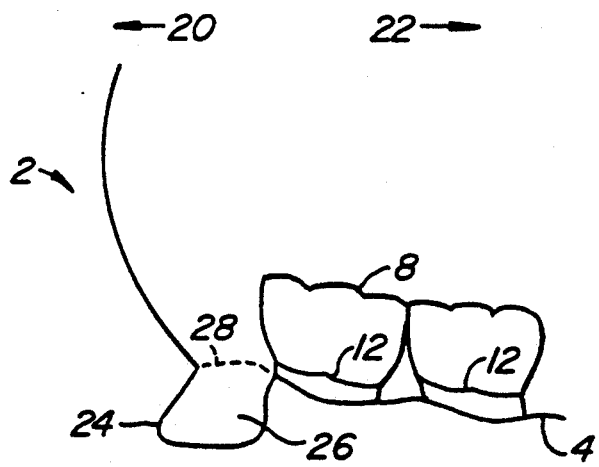
FIG. 2 is a schematic showing a bony deficit after removal of an impacted wisdom tooth.

After surgical removal of wisdom tooth 6, a bony deficit 26 is left in mandible 2 as shown in FIG. 2. An abnormal bone line 24 is evident. An incised portion of mucosal tissue 28 may partially cover deficit 26. A mechanical barrier 36 of dimensions appropriate to cover deficit 26 is placed over deficit 26. This placement typically occurs contemporaneously with the surgical procedure responsible for surgical removal of wisdom tooth 6, but may occur at another time in some cases. The patient might be under general anesthesia or sedation during the procedure, but a local anesthetic is also appropriate. After it is properly positioned, barrier 36 is secured in place.

Barrier 36 is preferably formed out of a resorbable material. Examples include biodegradable ceramics, modified starches or gelatins, polyamides, and resorbable polymers such as polymers of glycolic or lactic acid. Alternatively, barrier 36 could be formed of a nonresorbable material such as polytetrafluoroethylene, or PTFE or expanded PTFE, which is marketed under the tradename GORE-TEX TM. Other fluoroplastics or fibrous fabric materials could also be used. Additionally, barrier 36 may be made of a cellulose membrane filter such as MILLIPORE TM. The dimensions of barrier 36 vary with the clinical requirements.

Figure 3A:
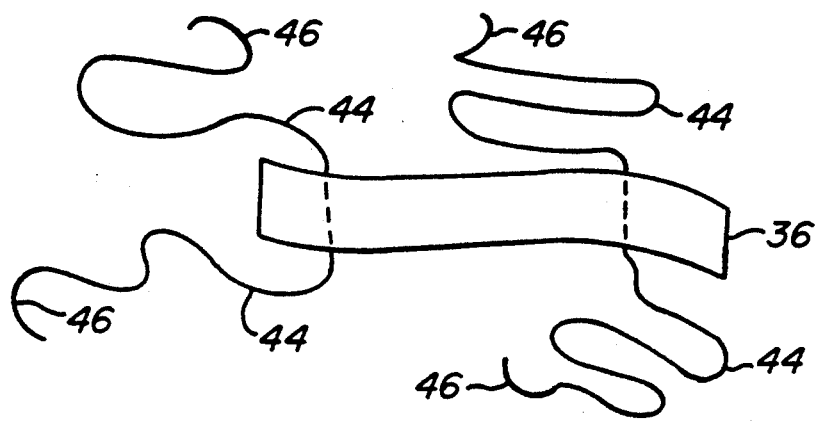
FIG. 3A-B is a device constructed in accordance with the present invention showing a barrier with anchoring sutures.
Figure 3B:
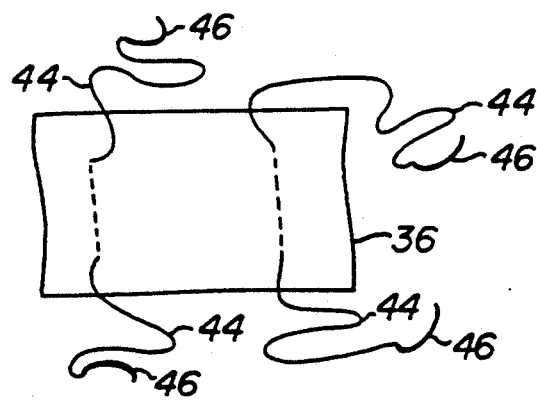

Barrier 36 is secured into position by any of a number of means. For example, barrier 36 may be stitched in place with suture which is either resorbable or nonresorbable, single filament or multi-filament. Suture materials and needles are well known in the art. FIG. 3A is a side view of barrier 36. Suture material 44 is swaged or placed through two locations of barrier 36, preferably near two ends. Each suture 44 is supplied with a pair of swaged or fused-on needles 46. A top view of barrier 36 with suture material 44 and needles 46 is sketched in FIG. 3B.

Other arrangements of sutures 44 and needles 46 are apparent; for instance, the numbers and location could vary. Needle 46 may be provided separately from suture 44 instead of being swaged or a single needle 46 may be used instead of pairs.

Alternative means of securing the barrier include a pincers arrangement. In one configuration the pincers fit around the back of a nearby tooth. The pincers may be opened and applied with a special tool-like device. Another form of pincers are anchored with sutures which would tie into the wound or around adjacent tooth. The pincers could be springloaded and would preferably be made of polyvinyl. Alternatively, the pincers could be formed from a resorbable material, such as a polysaccharide, having an inherent resilience or springiness. Thus, the pincers could be wrapped around a tooth, e.g., a second molar, and act as an anchoring device. An alternative embodiment provides metal pincers.

Figure 4A:
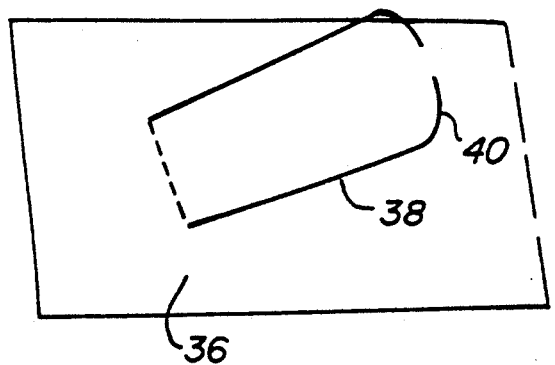
FIG. 4A is device constructed in accordance with the present invention showing a barrier with pincers-clamp anchor.
Figure 4B:
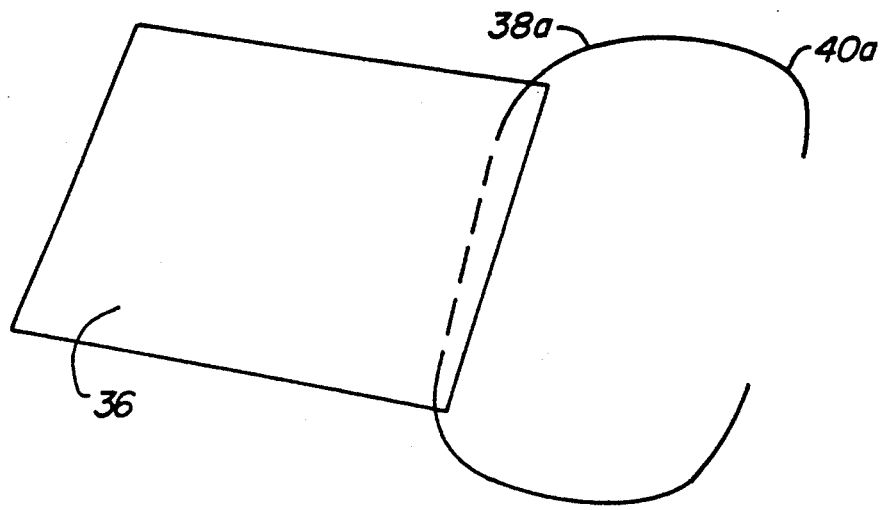
FIG. 4B is a device constructed in accordance with the present invention showing a support foot or ridge.

A simplified pincer 38 is shown in FIG. 4. A terminal portion of pincer 38 is bent or crimped to form arms 40 which engage a tooth to secure barrier 36. Arms 40 are placed around a tooth at an interproximal space 14.

In use, barrier 36 is slipped into the wound to cover bony defect 26. If using suture 44 to secure barrier 36, needle 46 is brought underneath flap 28 and pushed outward through the flap tissue. Each needle 46 pierces its respective portion of flap 28. When suture 44 is tied together, the edges of flap 28 are approximated. Barrier 36 is interposed between overlying soft tissue and underlying bony tissue.

If flap 28 has insufficient tissue to stitch or at the discretion of the surgeon, suture 44 could alternatively be wrapped around molar 8, brought to interproximal region 14, tied off and held in this position. Additional stabilizing sutures may be placed to stabilize this position. If barrier 36 is formed of a nonresorbable material, it is surgically removed after sufficient bony regeneration.

Bone substitute materials, which are known to the art, may be used in conjunction with this invention. Some examples of these materials are hydroxyapatite, powdered bone, calcium carbonate, freeze-dried bone, autologous bone, and various types of grafts. These materials may be placed into the deficit or socket area. For example, if the surgeon were treating a periodontal defect, the diseased area could be debrided and grafted. The barrier would be placed on top of the graft to protect it. Additionally, the invention could be used with other types of materials such as a fillers.

Further, the barrier is useful to protect a blood clot which forms after a surgical procedure. By protecting this blood clot, i.e., by covering the clot, the barrier would help prevent a condition called osteitis, commonly called "dry socket." Dry socket is painful and it occurs when the blood clot becomes gelatinous and lysis from the open wound. Thus, the bone is exposed to bacterial invasion from the oral cavity. The invention may facilitate prevention of advancing periodontal disease, gum disease, tissue dehiscence or loss of bone, especially after a third molar is removed or in conjunction with orthognathic surgery, periodontal surgery, or jaw surgery.

The invention is preferably packaged in sterile kits including the barrier and an anchoring means. As discussed, the anchoring means may be suture material, typically including a swaged-on needle, or an alternative pincer arrangement. Additionally, a kit may provide a barrier having one type of anchoring means at one end and an alternative type of anchor at its other end. After deciding which type of anchor to use, the surgeon would simply snip off and discard the undesired anchor.

Although it is contemplated that the invention will find most application in third molar areas, modifications of the invention can be otherwise utilized. For example, the device and method could be used to cover edentulous or tooth-bearing ridges in an attempt to maintain levels of bone or in an attempt to regraft levels of bone. Additionally, the invention may be useful in other medical settings such as in orthopedic surgery. The attachment or securing systems could be made larger or smaller, as indicated. Sutures or other anchoring means could be placed at both ends or other locations of the barrier in order to protect grafts of long bones, hip grafts, cervical grafts and other orthopedic procedures associated with bone deficits.

Because one of ordinary skill in the art would reasonably find workable modifications and variations of this invention, the invention is not to be limited by the foregoing description but rather by the scope of the following claims.

What is claimed is:

1. A method to facilitate tissue guided regeneration of a bony deficit of a bone using a mechanical barrier sized to cover said deficit comprising:
   a. placing the barrier over the deficit and beneath the periostium of the bone;
   b. shaping the barrier to the deficit; and
   c. securing the barrier in place.

2. The method of claim 1 wherein step (c) comprises suturing.

3. The method of claim 1 wherein step (c) comprises installation of a harness adapted to engage a permanent natural or modified structure associated with the bone, tooth orthodontic bracket or implant.

4. The method of claim 1 further comprising:

a. allowing bony regeneration at the site of the deficit; and
b. removing the barrier after bony regeneration has occurred.

5. A method of facilitating tissue guided regeneration of a mandibular bony deficit associated with removal of a molar from the mandible using a mechanical-biological barrier adapted to cover the deficit comprising:
   a. covering the deficit with the barrier;
   b. placing the barrier beneath the periostium of the mandible;
   c. shaping the barrier to the deficit; and
   d. securing the barrier in place.

6. A method of tissue guided regeneration to prevent osteitis of a bone after a surgical procedure resulting in a blood clot on a bone surface using a mechanical barrier dimensioned to cover the clot on the bone surface comprising:
   a. placing the barrier on the clot; and
   b. securing the barrier in place.

7. The method of claim 6 further comprising:
   a. allowing bony regeneration at the site of the clot; and
   b. removing the barrier after bony regeneration has occurred.

* * * * *